United States Patent
Huibregtse et al.

(10) Patent No.: US 10,758,655 B2
(45) Date of Patent: Sep. 1, 2020

(54) SYSTEMS AND METHODS TO REDUCE INJURY IN THE HEART

(71) Applicant: Cardiac Pacemakers, Inc., St. Paul, MN (US)

(72) Inventors: Barbara Ann Huibregtse, Westborough, MA (US); Thomas John Herbst, Coon Rapids, MN (US); Craig Stolen, New Brighton, MN (US); Eric M. Schneider, Cumberland, RI (US); Lynne E. Swanson, Edina, MN (US); Lili Liu, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 83 days.

(21) Appl. No.: 15/674,911

(22) Filed: Aug. 11, 2017

(65) Prior Publication Data
US 2018/0043071 A1     Feb. 15, 2018

Related U.S. Application Data

(60) Provisional application No. 62/373,631, filed on Aug. 11, 2016.

(51) Int. Cl.
*A61N 1/36*     (2006.01)
*A61M 1/12*     (2006.01)
(Continued)

(52) U.S. Cl.
CPC ............ *A61M 1/122* (2014.02); *A61M 5/142* (2013.01); *A61M 5/14276* (2013.01);
(Continued)

(58) Field of Classification Search
None
See application file for complete search history.

(56) References Cited

U.S. PATENT DOCUMENTS

| 7,092,753 | B2 | 8/2006 | Darvish et al. |
| 7,294,334 | B1 * | 11/2007 | Michal ................ A61K 9/0024 424/93.1 |

(Continued)

OTHER PUBLICATIONS

"Protecting Mitochondrial Bioenergetic Function during Resusitation from Cardiac Arrest", Crit. Care Clin. 28 (2), (Apr. 2012), 2 pgs.

(Continued)

*Primary Examiner* — Erica S Lee
(74) *Attorney, Agent, or Firm* — Schwegman Lundberg & Woessner, P.A.

(57) ABSTRACT

This document discusses, among other things, systems and methods to reduce ischemic or metabolic injury to a patient's heart. A system to reduce ischemic or metabolic injury to a patient's heart may include a pulse generator for generating electrical pulses or shock, a pacing lead with at least one pacing electrode configured to deliver electrical pulses received from the pulse generator to the patient's heart, a controller configured to control timing of electrical pulses to reduce wall stress of the heart, and a reservoir, fluidically coupled to a lumen and a pump, wherein the pump is configured, under control of the controller, to move contents from the reservoir through the lumen to an area of the heart with the reduced wall stress, wherein the contents include autologous respiration-competent mitochondria or other respiratory-promoting agents.

17 Claims, 5 Drawing Sheets

(51) Int. Cl.
*A61N 1/37* (2006.01)
*A61M 5/172* (2006.01)
*A61M 5/142* (2006.01)
*A61B 5/0205* (2006.01)
*A61M 1/10* (2006.01)

(52) U.S. Cl.
CPC ......... *A61M 5/172* (2013.01); *A61N 1/36175* (2013.01); *A61N 1/37* (2013.01); *A61B 5/0205* (2013.01); *A61M 1/1086* (2013.01); *A61M 2205/50* (2013.01)

(56) References Cited

U.S. PATENT DOCUMENTS

| | | | |
|---|---|---|---|
| 8,078,287 B2 | 12/2011 | Liu et al. | |
| 2005/0288721 A1* | 12/2005 | Girouard | A61M 5/14276 607/9 |
| 2006/0041276 A1* | 2/2006 | Chan | A61M 5/14276 607/3 |
| 2007/0088244 A1* | 4/2007 | Miller | A61B 17/3478 604/21 |
| 2007/0100383 A1* | 5/2007 | Pastore | A61N 1/0587 607/9 |
| 2007/0233216 A1 | 10/2007 | Liu et al. | |
| 2009/0255801 A1* | 10/2009 | Haas | G01N 33/4836 204/164 |
| 2010/0114284 A1* | 5/2010 | Doerr | A61N 1/057 607/120 |
| 2011/0008310 A1* | 1/2011 | Cataldo | A01K 67/0271 424/94.4 |
| 2013/0096639 A1* | 4/2013 | Ben-Haim | A61N 1/14 607/11 |
| 2013/0190834 A1* | 7/2013 | Ghosh | A61N 1/36592 607/17 |

OTHER PUBLICATIONS

Herbst, Thomas J., et al., "Methods for Producing Cardiomyocyte Cells", U.S. Appl. No. 62/206,845, filed Aug. 18, 2015.
Huibregtse, Barbara, et al., "Adjunctive Therapy Delivery Using a DBS Lead", U.S. Appl. No. 62/326,875, filed Apr. 25, 2016.
Masuzawa, Akihiro, et al., "Transplantation of autologously derived mitochondria protects the heart from ischemia-reperfusion injury", Am J. Physiology; Heart and Circulatory Physiology, (2013), 1-34.
McCully, James, et al., "Mitochondrial transplantation for theraputic use", Clinical and Translational Medicine 5:16, (2016), 13 pgs.
Prinzen, Frits, et al., "Mapping of Regional Myocardial Strain and Work During Ventricular Pacing: Experimental Study Using Magnetic Resonance Imaging Tagging", Journal of the American College of Cardiology, vol. 33, No. 6, (1999), 1735-1742.

* cited by examiner

SYSTEMS AND METHODS TO REDUCE INJURY IN THE HEART

CLAIM OF PRIORITY

This application claims the benefit of priority under 35 U.S.C. § 119(e) of U.S. Provisional Patent Application Ser. No. 62/373,631, filed on Aug. 11, 2016, which is herein incorporated by reference in its entirety.

TECHNICAL FIELD

This document relates generally to a therapy for treating the heart with a combination of a respiration promoting agent and cardiac pacing.

BACKGROUND

The heart is the center of a person's circulatory system and includes an intrinsic electro-mechanical system for performing pumping functions. The left portions of the heart, including a left atrium (LA) and a left ventricle (LV), draw oxygenated blood from the lungs and pump it to body organs to provide the organs with their metabolic need for oxygen. The right portions of the heart, including a right atrium (RA) and a right ventricle (RV), draw deoxygenated blood from the body organs and pump it to lungs where the blood gets oxygenated. The myocardium of the heart contracts in a coordinated fashion to provide these pumping functions. In a normal heart, a sinoatrial (SA) node, the heart's natural pacemaker, generates intrinsic electrical pulses that propagate through an electrical conduction system of conductile cardiomyocytes to various regions of the heart to excite the contractile myocardial syncytium of the cardiac muscle. For example, intrinsic electrical pulses originating from the SA node propagate through an atrio-ventricular (AV) node that is in the interatrial membranous septum between the RA and LA. From the AV node, a specialized intrinsic conduction system is used by the electrical impulses to reach ventricular myocardial tissues, resulting in contraction activities of ventricles. This specialized conduction system includes the His bundle, the right and left conduction bundle branches that extend along the septum between the RV and LV, and the Purkinje fibers that contact the ventricular myocardial tissues. Coordinated delays of the propagations of the intrinsic electrical pulses in a normal electrical conduction system cause the various portions of the heart to contract in synchrony which results in efficient pumping functions. In addition, electrically conductile devices chronically placed in the right ventricular cavity may support endomyocardial trabecular growth which may contribute to an increase in cardiomyocyte mass and pumping function. In an example, the conductile devices may be placed in the right or left ventricular cavity to support endomyocardial trabecular growth.

Heart disease may damage cardiac tissue, resulting in a loss of contractile and conductile myocardial cells and thus an inefficient pumping function, which may lead to further cardiac tissue damage and reduced cardiac output. An electrical pacing therapy, such as cardiac resynchronization therapy (CRT) may be provided to compensate for the damaged cardiac tissue by providing electrical pulses to the heart. However, there remains a need to restore damaged cardiac tissue.

SUMMARY

Various embodiments disclosed herein treat the heart with autologous mitochondria or other respiration promoting agents to improve or slow the progression of regions of myocardial ischemia. Cardiac pacing has been shown to increase respiration and oxygen consumption in cardiac muscle, and the combination of an electrical pacing therapy and the delivery of autologous respiration-competent mitochondria may reduce the risk of further cardiac ischemia in a patient. The combination of an electrical pacing therapy device placed in a ventricle, the delivery of autologous respiration-competent mitochondria may restore or improve heart function through both metabolic support and de-novo myocardial cellular regeneration. In an example, the electrical therapy pacing device may be placed in coronary venous anatomy outside of a ventricle. For example, a patient having an arrhythmia, congestive heart failure, or myocardial infarction that is accompanied by a weakened cardiac wall function may receive at least one dose of autologous respiration-competent mitochondria delivered to the wall of the heart in combination with chronic lead placement (in the RV or LV cavities or both) and subsequent electrical pacing of the heart.

An example (e.g., "Example 1") of subject matter (e.g., system to reduce ischemic or metabolic injury to a patient's heart) may include a pulse generator for generating electrical pulses, a pacing lead with at least one pacing electrode configured to deliver electrical pulses received from the pulse generator to the patient's heart, a controller configured to control timing of electrical pulses to reduce wall stress of the heart, and a reservoir, fluidically coupled to a lumen and a pump, wherein the pump is configured, under control of the controller, to move contents from the reservoir through the lumen to an area of the heart with the reduced wall stress, wherein the contents include autologous respiration-competent mitochondria or other respiratory-promoting agents suspended in a solution.

In Example 2, the subject matter of Example 1 may optionally be configured such that the contents only include autologous respiration-competent mitochondria suspended in a buffered isotonic solution, isosmotic buffer or other respiratory substrate.

In Example 3, the subject matter of any one or any combination of Examples 1-2 may optionally be configured such that the controller is configured to increase an AV delay of the electrical pulses at least predetermined time interval after moving the contents to an area of the heart with reduced wall stress.

In Example 4, the subject matter of any one or any combination of Examples 1-3 may optionally be configured such that the predetermined time interval is at least 1 hour.

In Example 5, the subject matter of any one or any combination of Examples 1-4 may optionally be configured such that the lumen includes a plurality of perforations and the contents are moved through the plurality of perforations.

In Example 6, the subject matter of any one or any combination of Examples 1-5 may optionally be configured such that the pacing lead includes a helical screw and the contents are moved through a hollow lumen of the helical screw.

In Example 7, the subject matter of any one or any combination of Examples 1-6 may optionally include comprising a check valve configured to prevent the patient's blood from entering the proximal lumen of the catheter.

In Example 8, the subject matter of any one or any combination of Examples 1-7 may optionally include an insertable sheath configured to cover the lumen and prevent the patient's blood from entering the lumen.

In Example 9, the subject matter of any one or any combination of Examples 1-8 may optionally be configured such that the pacing lead is configured to promote and augment cellular regeneration or myocardiocyte growth initiated by the presence of the pacing lead or a defibrillation lead.

In Example 10, the subject matter of Example 9 may optionally be configured such that the pacing lead includes a microscopically etched surface.

In Example 11, the subject matter of Example 10 may optionally be configured such that the microscopically etched surface includes a pattern having a diameter in the range of 0.05 mm-1.0 mm.

In Example 12, the subject matter of any one or any combination of Examples 9-11 may optionally be configured such that the controller is configured to cause the pulse generator to provide an electrical waveform to the patient's cardiac tissue having the reduced wall stress to further promote cellular regeneration and/or myocardiocyte growth.

In Example 13, the subject matter of any one or any combination of Examples 9-12 may optionally be configured such that the cardiomyocyte growth includes conductile myocyte growth and/or contractile myocyte growth.

An example (e.g., "Example 14") of subject matter (e.g., system to reduce ischemic or metabolic injury to a patient's heart) may include a pulse generator for generating electrical pulses, at least one pacing electrode configured to deliver electrical pulses received from the pulse generator to the patient's heart, a controller configured to control timing of electrical pulses to reduce wall stress of the heart, and a pump configured, under control of the controller, to move contents to an area of the heart with the reduced wall stress, wherein the contents include autologous respiration-competent mitochondria or other respiratory-promoting agents.

In Example 15, the subject matter of Examples 1-14 may optionally be configured such that the controller and pulse generator are configured to deliver a cardiac resynchronization therapy to the patient.

An example (e.g., "Example 16") of subject matter (e.g., system to reduce ischemic or metabolic injury to a patient's heart) may include a pulse generator for generating electrical pulses, a pacing lead with at least one pacing electrode configured to deliver electrical pulses received from the pulse generator to the patient's heart, a controller configured to control timing of electrical pulses to reduce wall stress of the heart, and a reservoir, fluidically coupled to a lumen and a pump, wherein the pump is configured, under control of the controller, to move contents from the reservoir through the lumen to an area of the heart with the reduced wall stress, wherein the contents include autologous respiration-competent mitochondria or other respiratory-promoting agents suspended in a buffered isotonic solution, isosmotic buffer or other respiratory substrate.

In Example 17, the subject matter of Example 16 may optionally be configured such that the contents only include autologous respiration-competent mitochondria suspended in a solution.

In Example 18, the subject matter of Example 17 may optionally be configured such that the controller is configured to increase an AV delay of the electrical pulses at least predetermined time interval after moving the contents to an area of the heart with reduced wall stress.

In Example 19, the subject matter of Example 17 may optionally be configured such that the lumen includes a plurality of perforations and the contents are moved through the plurality of perforations.

In Example 20, the subject matter of Example 17 may optionally be configured such that the pacing lead includes a hollow core helical screw and the contents are moved through a hollow bore of the helical screw.

In Example 21, the subject matter of Example 17 may optionally include a check valve configured to prevent the patient's blood from entering the lumen.

In Example 22, the subject matter of Example 17 may optionally include an insertable sheath configured to cover the lumen and prevent the patient's blood from entering the lumen.

In Example 23, the subject matter of Example 17 may optionally be configured such that the pacing lead is configured to promote and augment cellular regeneration or myocardiocyte growth initiated by the presence of the pacing lead.

In Example 24, the subject matter of Example 17 may optionally be configured such that the pacing lead includes a microscopically etched surface.

In Example 25, the subject matter of Example 24 may optionally be configured such that the microscopically etched surface includes a pattern having a diameter in the range of 0.05 mm-1.0 mm.

An example (e.g., "Example 26") of subject matter (e.g., method) may include treating a cardiac condition by providing a respiratory promoting agent and providing electrical pacing to a patient's heart via a pulse generator having a pacing lead including a pacing electrode, wherein treating the cardiac condition may include generating electrical pulses, delivering the electrical pulses to cardiac tissue of the patient via the pacing electrode to reduce wall stress in the patient's heart, and providing the respiratory promoting agent to the patient's cardiac tissue having the reduced wall stress to provide enhanced respiration of the patient's heart.

In Example 27, the subject matter of Example 26 may optionally be configured such that the respiratory promoting agent includes autologous respiration-competent mitochondria.

In Example 28, the subject matter of Example 27 may optionally be configured such that treating the cardiac condition further comprises increasing an AV delay of the electrical pulses at least one predetermined time interval after providing autologous respiration-competent mitochondria to the patient's cardiac tissue having the reduced wall stress.

In Example 29, the subject matter of Example 27 may optionally include providing a diluent or adjuvant to the implanted reservoir to preserve the respiration-competent mitochondria.

In Example 30, the subject matter of Example 27 may optionally include delivering a cardiac resynchronization therapy to the patient.

In Example 31, the subject matter of Example 27 may optionally be configured such that the autologous mitochondria are provided to promote and augment cellular regeneration and/or myocardiocyte growth initiated by the presence of the pacing lead.

In Example 32, the subject matter of Example 27 may optionally be configured such that the autologous mitochondria are provided by at least two endocardial injection sites to increase the density of de novo trabecular cardiomyocyte fiber growth.

In Example 33, the subject matter of Example 27 may optionally be configured such that the pacing lead is configured to promote de novo trabecular fiber attachment.

In Example 34, the subject matter of Example 27 may optionally include providing an electrical waveform to the patient's cardiac tissue having the reduced wall stress to further promote cellular regeneration or myocardiocyte growth.

In Example 35, the subject matter of Example 27 may optionally include a pacing lead that may include a lumen configured to deliver a respiratory promoting agent.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Various examples provide pacing pulses to reduce wall stress of the heart, and deliver a respiratory promoting agent to the area of the heart having the reduced stress to restore damaged cardiac tissue or to improve the condition of the cardiac tissue.

Figure 1:
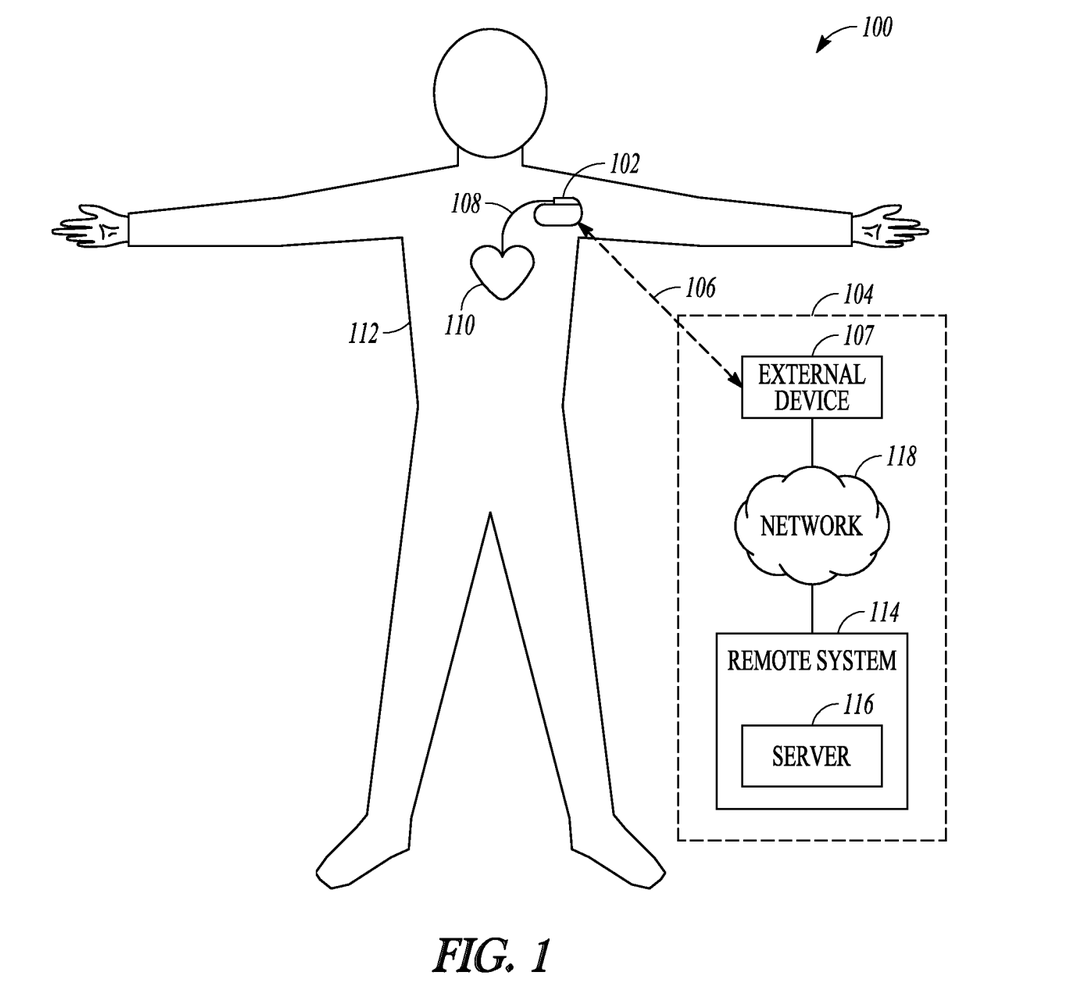
FIG. 1 illustrates an example of a cardiac treatment system.

FIG. 1 illustrates an example of a cardiac treatment system 100. An example of the cardiac treatment system 100 may be configured to include an implantable medical device (IMD) 102, an external system 104, and a communication link such as a telemetry link 106. The IMD 102 may include an electronic unit coupled by a cardiac lead 108, or additional leads, to a heart 110 of a subject 112. The IMD 102 may additionally include a reservoir 240 coupled by cardiac lead 108 or additional leads to the heart 110 of the subject 112. Examples of the IMD 102 may include, but are not limited to, pacemakers, pacemaker/defibrillators, cardiac resynchronization devices, cardiac remodeling control devices, and cardiac monitors. In an example, the IMD 102 may be configured to monitor health of the heart 110 and determine one or more abnormalities associated with the heart 110. The IMD 102 may take an action, such as stimulating one or more portions of the heart 110 through the lead 108 and delivering a therapeutic agent to the heart 110 through the lead 108. In an example, the therapeutic agent may be autologous, respiration-competent mitochondria that reduce ischemic or metabolic injury to a patient's heart.

In an example, the external system 104 may include an external device 107 configured to communicate bi-directionally with the IMD 102 such as through the telemetry link 106. For example, the external device 107 may include a programmer to program the IMD 102 to provide one or more therapies to the heart 110. In an example, the external device 107 may program the IMD 102 to provide a therapeutic agent and cardiac resynchronization therapy (CRT) to the heart 110.

In an example, the external device 107 may be configured to transmit data to the IMD 102 through the telemetry link 106. Examples of such transmitted data may include programming instructions for the IMD 102 to acquire physiological data, perform at least one self-diagnostic test (such as for a device operational status), or deliver at least one therapy or any other data. In an example, the IMD 102 may be configured to transmit data to the external device 107 through the telemetry link 106. This transmitted data may include real-time physiological data acquired by the IMD 102 or stored in the IMD 102, therapy history data, an operational status of the IMD 102 (e.g., battery status or lead impedance), and the like. In an example, the telemetry link 106 may include an inductive telemetry link or a far-field radio-frequency telemetry link.

In an example, the external device 107 may be a part of a patient management system that may include other devices such as a remote system 114 for remotely programming the IMD 102. In an example, the remote system 114 may be configured to include a server 116 that may communicate with the external device 107 through a telecommunication network 118 such as to access the IMD 102 to remotely monitor the health of the heart 110 or adjust parameters associated with the one or more therapies.

Figure 2:
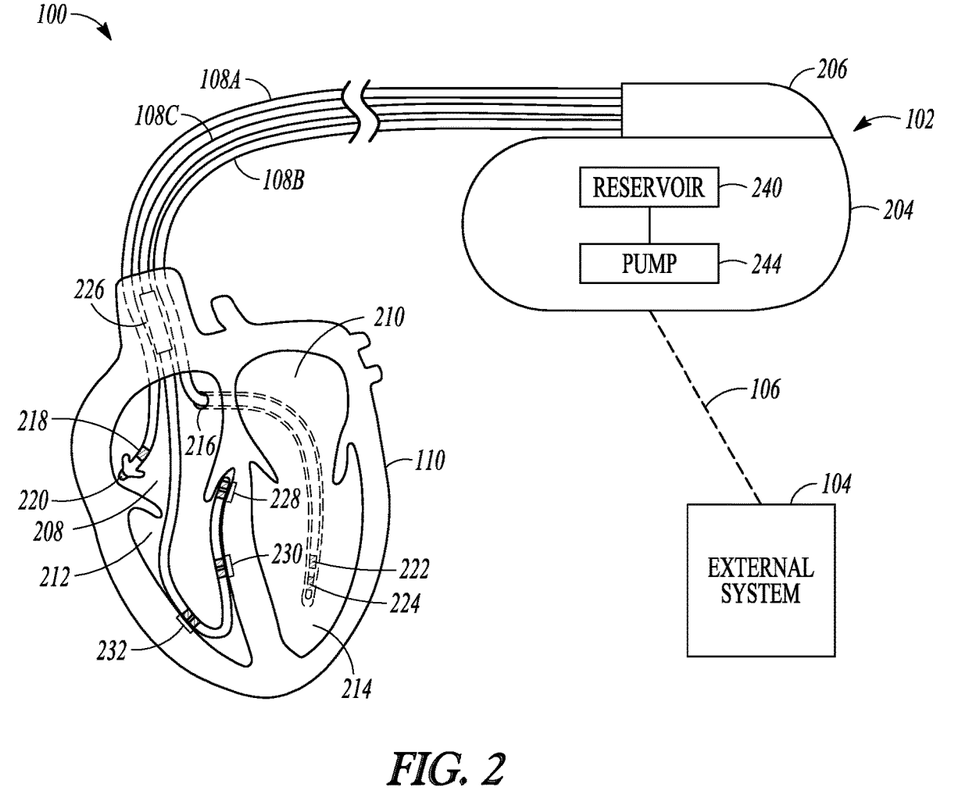
FIG. 2 illustrates an example of portions of the cardiac treatment system.

FIG. 2 illustrates an example of portions of the cardiac treatment system. In an example, the IMD 102 of the cardiac treatment system 100 may include a hermetically-sealed housing 204 and a header 206 that extends from the housing 204. The header 206 may include one or more receptacles such as for receiving proximal ends of one or more leads such as a lead 108A, a lead 108B and a lead 108C (collectively referred to herein as leads 108). Distal ends of the leads 108 may be coupled to electrodes such as for providing pacing energy, defibrillation energy, or both, in conjunction with the electrodes disposed on or around the heart 110. The electrodes may also be used for sensing electrical activity of the heart 110, including electrical activity related to contractions of the atria or ventricles. The leads 108 may include a lumen for delivering a therapeutic agent to the heart 110. The IMD 102 may also include a reservoir 240 for storing the therapeutic agent and a pump 244 for delivering the therapeutic from the reservoir 240 to the heart 110 via the lumen.

As shown in FIG. 2, the heart 110 includes a right atrium (RA) 208, a left atrium (LA) 210, a right ventricle (RV) 212, a left ventricle (LV) 214, and a coronary sinus 216 extending from the RA 208. In an example, lead 108A may be an intravascular RA lead that may extend from a superior vena cava (SVC) into the RA 208 and may include electrodes such as a ring electrode 218 and a tip electrode 220 such as for sensing signals, or delivering pacing therapy, or both, to the RA 208. In an example, the lead 108A may also include a lumen for delivering a therapeutic agent to the heart 110 with or without the delivery of a pacing therapy. In an example, lead 108B may be an intravascular coronary sinus (CS)/left ventricle (LV) lead that may extend into the LV 214 through the CS 216. In an example, the LV lead 108B may include ring electrodes 222 and 224 through which intrinsic electrical heart signals may be sensed. In an example, the lead 108B may also include a lumen for delivering a therapeutic agent to the heart 110. In an example, electro-stimulation energy and a therapeutic agent may be delivered using the LV lead.

In an example, lead 108C may be an intravascular right ventricle (RV) lead that may extend from the SVC into the RA 208, and then into the RV 212. The lead 108C may be configured to include a defibrillation coil electrode 226 such as to provide high energy shock therapy to the subject. The RV lead 108C may include a plurality of electrode pairs such as an electrode pair 228, electrode pair 230, and electrode pair 232 for sensing signals, delivering pacing therapy, or both. In an example, the RV lead 108C may also include a lumen for delivering a therapeutic agent to the heart 110. The RV lead 108C may be configured to achieve resynchronization of the RV 212.

The present methods, devices and systems may work in a variety of electrode configurations and with a variety of electrodes. In an example, the different implantable electrode configurations may be defined by various combinations of electrodes. The electrodes may be used to deliver cardioversion, defibrillation, pacing, or resynchronization therapy, or combinations thereof to at least one chamber of the heart 110.

In an example, the IMD 102 may be configured to select at least one electrode pair from a plurality of electrode pairs of the RV lead 108C and deliver an electrical stimulation pulse through the selected electrode pair and also deliver a therapeutic agent through the lumen. A selective stimulation of the one or more portions of the RV 212 as part of CRT may synchronize contraction of the RV 212 and LV 214 and thereby improve the performance of the hemodynamic system of the subject 112. The synchronization may reduce wall stress and provide a more hospitable location for the mitochondria.

Figure 3:
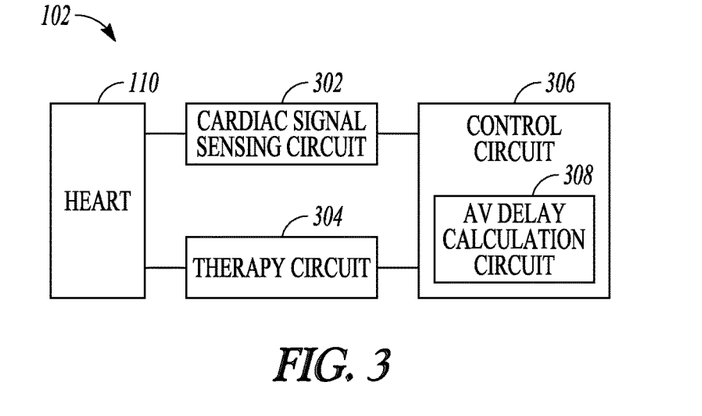
FIG. 3 illustrates an example of portions of an implantable medical device (IMD) of the cardiac treatment system of FIGS. 1 and 2.

FIG. 3 illustrates an example of portions of an implantable medical device (IMD) of the cardiac treatment system of FIGS. 1 and 2. In an example, the IMD 102 may be configured to include a cardiac signal sensing circuit 302, a therapy circuit 304, and a control circuit 306. The control circuit 306 may be configured to communicate with the cardiac signal sensing circuit 302 and therapy circuit 304 to provide a cardiac treatment therapy including delivery of electrical pacing and a therapeutic agent to the heart 110. The control circuit 306 may communicate electrical signals with the cardiac signal sensing circuit 302 and the therapy circuit 304 even though there may be intervening circuitry between the control circuit 306, the cardiac signal sensing circuit 302, and the therapy circuit 304.

In an example, the cardiac signal sensing circuit 302 senses an intrinsic depolarization event in an atrium of the subject. The cardiac signal sensing circuit 302 may sense the atrium depolarization event using one or more signals as determined from the electrodes (e.g., the ring electrode 218 or the tip electrode 220 in FIG. 2). In an example, the one or more signals may be an impedance vector signal, pressure signal, contraction pattern, electrocardiogram (EGM) signal or any other signal. As described previously herein, the IMD 102 may be electrically coupled to electrodes such as the electrode pair 228, electrode pair 230, and electrode pair 232 that are implantable within the heart 110 through the RV lead 108C. The electrode pair 228 may be placed at a location in the right branch of the His bundle of the subject 112. The therapy circuit 304 may be electrically connected to a first electrode pair, such as electrode pair 228, to deliver an electrical stimulation pulse to the His bundle region of the heart 110. In an example, the electrode pair 228 may be disposed in the His bundle region in a manner such that the stimulation location is distal to a location of the conduction block in the right branch of the His bundle.

In an example, the control circuit 306 may include a processor (e.g., a microprocessor digital signal processor, application specific integrated circuit (ASIC) or other type of processor) interpreting or executing instructions in software modules or firmware modules. The control circuit 306 may include other circuits or sub-circuits to perform the function described. These circuits may include software, hardware, firmware, or any combination thereof. The control circuit 306 includes an AV delay calculation circuit 308 that may calculate an optimal value for a paced AV delay interval. The regional contribution to each cardiac cycle may be modified by changing the AV delay. When shortening the AV delay, the work done by the region closest to the lead delivering the electrical pacing therapy is reduced because the region begins contracting against a reduced preload. This is the opposite situation that occurs when damage is present and regional activation is delayed, leading to increased work because the region is stretched and contracts against increased ventricular pressure. In an example, by optimizing the AV delay, the tissue stress around the lead may be lowered so that when the mitochondria are injected through the lead they arrive in a more hospitable niche that may be more amenable to their integration. As the mitochondria incorporate into the tissue and begin contributing to the local energy production, the amount of work performed by the region around the lead may be slowly increased, by lengthening the AV delay, thus achieving a more natural contraction pattern. In an example, the AV delay may be decreased prior to the delivery of mitochondria. Then after a predetermined time interval has elapsed after delivery of the mitochondria, the AV delay may then be gradually increased such that the targeted ischemic region may be synchronized to emulate healthy contractions and the target area may again contribute work to the cardiac contraction. In some examples, the predetermined time interval is at least one hour.

An example of the control circuit may be further configured to control pump 244 to cause a therapeutic agent to be delivered from the reservoir 240 to the heart 110. In an example, the therapeutic agent is delivered to the heart after the delivery of electrical pulses associated with an electrical pacing therapy. In an example, the therapeutic agent may be injected directly into ischemic heart tissue endocardially. In an example, the therapeutic agent may be injected retrograde via the small cardiac vein epicardially by temporarily or permanently occluding the small coronary vein. The coronary vein occlusion may be achieved by wedging the lead tip or inflatable/deflectable balloon/SES assembled on the lead body, or some expandable material proximal to the lead tip. In an example, the therapeutic agent may be injected one time, or multiple times.

Figure 4A:
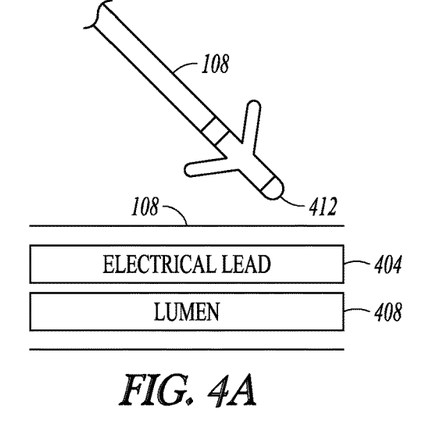
FIGS. 4A-4C illustrate examples of leads in the cardiac treatment system of FIGS. 1 and 2.

FIG. 4A illustrates an example of a lead in the cardiac treatment system of FIGS. 1 and 2.

In an example, the lead 108 includes an electrode 412 at a distal end, an electrical lead 404, and a lumen 408. The electrical lead 404 may electrically couple the electrode 412 to the control circuit 306. The lumen 408 may be configured to enable the contents of the reservoir 240 to move from the reservoir 240, through the lumen 408, and to the heart 110. In an example, the lead 108 may include a sensor (e.g., a position sensor). In an example, the reservoir 240 may include a terminal pin and the reservoir may be refilled manually with a syringe, such as through the terminal pin.

Figure 4B:
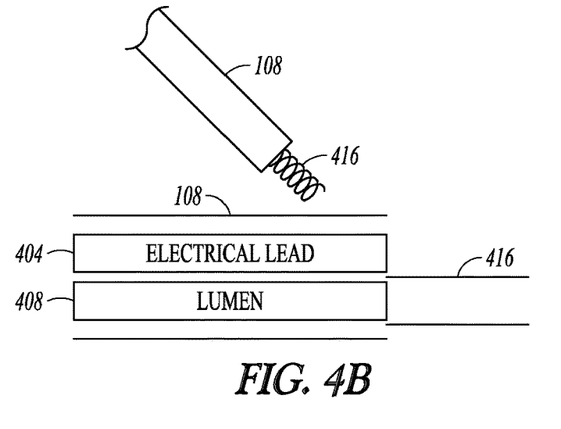

FIG. 4B illustrates an example of a lead in the cardiac treatment system of FIGS. 1 and 2.

In an example, the lead 108 includes a helical screw 416 at a distal end, an electrical lead 404, and a lumen 408. The electrical lead 404 may electrically couple the helical screw 416 to the control circuit 306. The lumen 408 may be configured to enable the contents of the reservoir 240 to move from the reservoir 240, through the lumen 408, and to the heart 110. In an example, the lead 108 may include a sensor (e.g., a position sensor). In an example, the helical screw may be part of the fixation portion of the lead or a stylet and the stylet may have a working lumen configured to inject a therapeutic agent to the heart 110. In an example, the helical screw 416 may include a hollow bore configured to receive contents from the lumen 408 and deliver contents of the reservoir to the heart 110. In an example, the electrical lead 404 may be electrically connected to the helical screw 416. In an example, the lumen may pass through the hollow bore of the helical screw 416. In an example, a diameter of the hollow bore may be in the range of 100 to 500 μm.

Figure 4C:
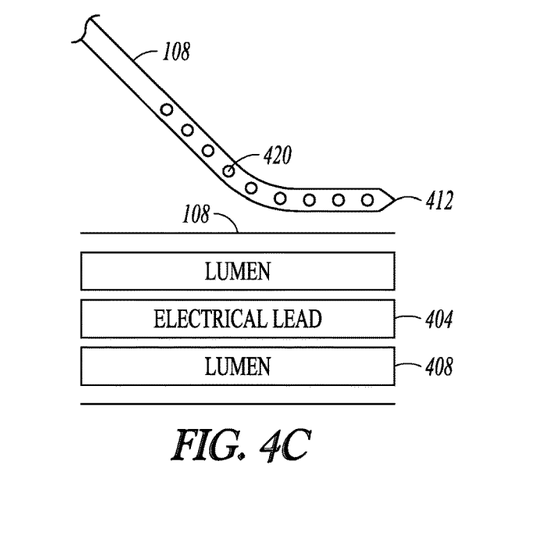

FIG. 4C illustrates an example of a lead in the cardiac treatment system of FIGS. 1 and 2.

In an example, the lead 108 includes an electrode 412 at a distal end, an electrical lead 404, and a perforated lumen 420. The electrical lead 404 may electrically couple the electrode 412 to the control circuit 306. The perforated lumen 420 may include at least one opening along a length thereof and may be configured to enable the contents of the reservoir 240 to move from the reservoir 240, through the lumen 408, and to the heart 110. The at least one opening along the length of the perforated lumen 420 may deliver fluid from the reservoir to a location adjacent to the at least one opening. In an example, the lead 108 may include a sensor (e.g., a position sensor).

Figure 5A:
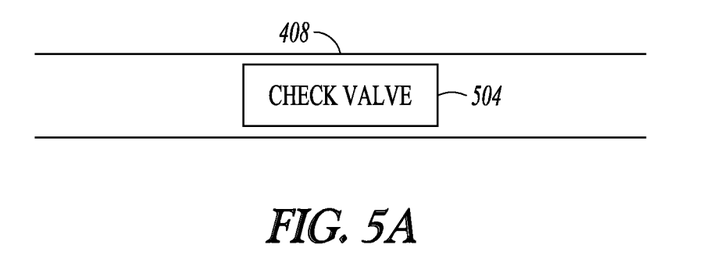
FIGS. 5A-5B illustrate examples of lumens associated with the leads shown in FIGS. 4A-4C.

FIG. 5A illustrates an example of a lumen associated with the leads shown in FIGS. 4A-4C. In an example, the lumen 408 includes a check valve 504 that is configured to prevent a flow of blood from entering the lumen 408, pump 244 and reservoir 240. In an example, the check valve 504 may be located at a distal end of the lumen 408. In an example, the check valve may be located at a proximal end of the lumen 408. In an example, the check valve may be located at any position along the length of the lumen 408.

Figure 5B:
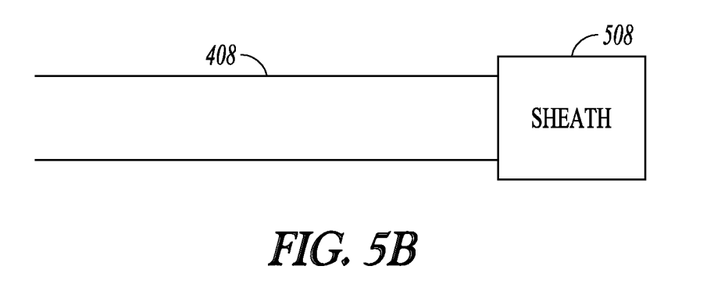

FIG. 5B illustrates an example of a lumen associated with the leads shown in FIGS. 4A-4C. In an example, the lumen 408 includes a sheath 508 that is configured to prevent a flow of blood from entering the lumen 408, pump 244 and reservoir 240.

Figure 6:
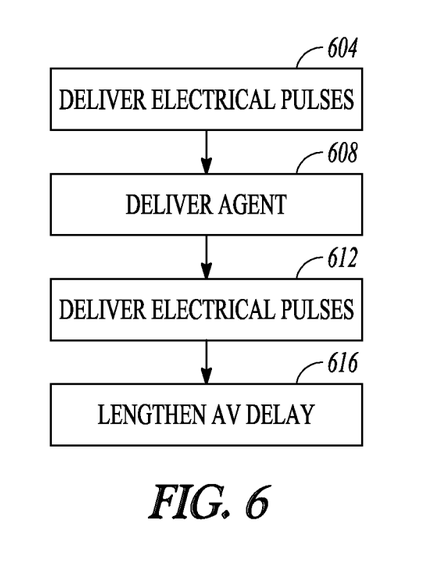
FIG. 6 illustrates an example for operating a cardiac treatment system to treat ischemic or metabolic injury in the heart.

FIG. 6 illustrates an example for operating a cardiac treatment system to treat ischemic or metabolic injury in the heart. In an example, the cardiac treatment system 100 is operated to provide a therapy for treating the heart with a combination of a respiration promoting agent and cardiac pacing. In an example, the cardiac treatment system 100 is operated to provide a therapy for treating the heart with a combination of a respiration promoting agent and cardiac pacing. At 604, the method may include delivering an electrical pacing therapy via a lead 108 to a patient's heart 110. In an example, the electrical pacing therapy is delivered without the use of a lead. In an example, the electrical pacing therapy has an AV delay and is configured to cause the region proximal to the lead 108 to contract against a reduced preload, thereby reducing the cardiac tissue stress proximal to the lead 108. In an example, the electrical pacing therapy may be a cardiac resynchronization therapy. At 608, the method may include delivering a respiration promoting agent to the region proximal to the lead 108 where the cardiac tissue stress has been reduced by the electrical pacing therapy. In an example, the respiration promoting agent is delivered from a reservoir to the region proximal to the lead 108 where the cardiac tissue stress has been reduced by the electrical pacing therapy. In an example, the respiration promoting agent is delivered to a localized region of the patient's heart 110. In an example, the respiration promoting agent may be autologous respiration-competent mitochondria. In an example, the respiration promoting agent may be a protein or a gene. In an example, a shock therapy may be delivered during delivery of the respiration promoting agent. At 612, the method may include delivering additional electrical pacing therapy via lead 108 to the patient's heart 110. In an example, the additional electrical pacing therapy may be a cardiac resynchronization therapy. At 616, the method may include increasing the AV delay of the additional electrical pacing therapy as the mitochondria incorporate into the cardiac tissue and begin contributing to the local energy production. As the mitochondria begin contributing to the local energy production, the amount of work performed by the region around the lead may be slowly increased, by lengthening the AV delay, thus achieving a more natural contraction pattern. In an example, the AV delay is adjusted to minimize death of the delivered autologous respiration-competent mitochondria. In an example, the method may include sensing a condition of the heart via lead 108 and adjusting an electrical pacing therapy based thereon. In an example, the method may include providing a diluent or adjuvant to the reservoir that preserves the viability of the mitochondrial respiratory function for either long acting, continuous or a pulsed delivery of the respiration-competent mitochondria. In an example, the adjuvant may be corticosteroids such as prednisone, or dexamethasone or other. In some examples, the viability of the mitochondria may be essential (e.g., nonviable mitochondria may not be able to delay, prevent, or reduce myocardial injury). In an example, the reservoir may be permeable to allow the mitochondria contained in the reservoir to be sustained by native circulation. In some examples, respiration-competent mitochondria may be delivered from the reservoir at regular intervals or other programmed intervals. By way of example and not limitation, the respiration-competent mitochondria may be delivered hourly (or at intervals of about X hours where X is a variable that may be an integer or fraction) or may be delivered daily (or at intervals of about X days where X is a variable that may be an integer or fraction). In an example, an electrical current delivered during a defibrillation shock therapy may limit mitochondrial respiration. The limited mitochondrial respiration may be in response to at least one of hypoxia or reperfusion. The delivery of respiration-competent mitochondria may be concurrent with the defibrillation shock therapy. The respiration-competent mitochondria may be delivered to a focal region of the defibrillation shock therapy. In an example, the respiration-competent mitochondria may be delivered during a post shock window (e.g., within 1 minute after the defibrillation shock therapy, or within 30 seconds after the defibrillation shock therapy). The cardiac treatment system 100 may be programmed to automatically deliver the respiration competent mitochondria concurrently with the defibrillation shock therapy or during the post shock window.

Figure 7:
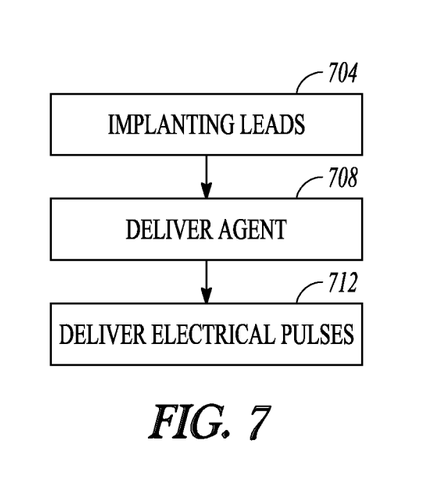
FIG. 7 illustrates and example for operating a cardiac treatment system to promote the growth of trabecular fibers in the heart.

FIG. 7 illustrates an example for operating a cardiac treatment system to promote the growth of trabecular fibers in the heart. In an example, the cardiac treatment system 100 is operated to provide enhanced growth of new cardiac mass in the patient's heart 110. In an example, the growth of new cardiac mass includes the growth of new trabecular fibers in the patient's right ventricle. In an example, a lead may be placed in the patient's left ventricle and a growth of new trabecular fibers occurs in the patient's left ventricle. At 704, the method may include implanting a lead in the patient's heart 110 to provide a local conduction disturbance to stimulate the growth of new cardiac mass. In an example the growth of new cardiac mass includes the growth trabecular fibers. In an example, the lead is implanted in the right ventricle of the heart 110. At 708, a respiration promoting agent may be delivered to the patient's heart 110, proximal to the implanted lead 108. In an example, the respiration promoting agent includes autologous respiration-competent mitochondria. The autologous respiration mitochondria may cause enhanced growth of new cardiac mass in the patient's heart 110. In an example, the lead is modified to promote de novo trabecular fiber attachment. Examples of lead modifications include adding additional electrodes as well as microscopic surface etching of the lead, where the surface etching forms a pattern on the lead and the pattern on the lead has a diameter similar to that of a small trabecula fiber (e.g., a diameter in the range of 0.05-1.0 mm). In an example, the lead includes multiple endocardial injection sites that are configured to deliver respiration-competent mitochondria to the patient's heart 110 and thereby increase the density of de novo trabecular fiber growth. At 712, the method may include delivering an electrical pacing therapy via lead 108 to the patient's heart 110. In an example, the delivery of electrical impulses or waveforms can provide additional de novo trabecular fiber attachment. In an example, the cardiomyocyte growth can include both conductile and contractile myocyte growth. The above detailed description is intended to be illustrative, and not restrictive. The scope of the disclosure should, therefore, be determined with references to the appended claims, along with the full scope of equivalents to which such claims are entitled.

What is claimed is:

1. A method performed using an implantable medical device including a pulse generator, a pacing lead with at least one pacing electrode, a controller, a lumen, a reservoir, and a pump, wherein the method comprises using the implantable medical device to treat a cardiac condition by providing a respiratory promoting agent at programmed intervals and providing electrical pacing to a patient's heart, wherein using the implantable medical device to treat the cardiac condition comprises:
   generating electrical pulses using the pulse generator;
   delivering the electrical pulses to cardiac tissue of the patient using the pacing lead, including controlling timing of the delivered electrical pulses to reduce wall stress during contraction in cardiac tissue proximate to the pacing electrode in the patient's heart, wherein the delivered electrical pulses cause the cardiac tissue to contract with an AV delay; and
   providing the respiratory promoting agent at the programmed intervals using the controller and the pump, from the reservoir through the lumen to the patient's cardiac tissue proximate to the pacing electrode, wherein the patient's cardiac tissue proximate to the pacing electrode, which has the reduced wall stress during contraction, is a more hospitable location for integration of the respiratory promoting agent with the cardiac tissue,
   wherein controlling timing of the delivered electrical pulses includes increasing the AV delay for a predetermined time interval each time when the respiratory promoting agent is provided to the patient's cardiac tissue.

2. The method according to claim 1, wherein the respiratory promoting agent includes autologous respiration-competent mitochondria.

3. The method according to claim 2, further comprising providing a diluent or adjuvant to the implanted reservoir to preserve the respiration-competent mitochondria within the implanted reservoir.

4. The method according to claim 2, further comprising delivering a cardiac resynchronization therapy to the patient.

5. The method according to claim 2, wherein the autologous mitochondria are provided to promote and augment cellular regeneration and/or myocardiocyte growth initiated by the presence of the pacing lead.

6. The method according to claim 2, wherein the autologous mitochondria are provided by at least two endocardial injection sites to increase the density of de novo trabecular cardiomyocyte fiber growth.

7. The method according to claim 2, wherein the pacing lead is configured to promote de novo trabecular fiber attachment.

8. The method according to claim 2, further comprising providing an electrical waveform to the patient's cardiac tissue having the reduced wall stress to further promote cellular regeneration or myocardiocyte growth.

9. The method of claim 2, wherein the pacing lead includes the lumen.

10. A method performed using an implantable medical device including a pulse generator, a pacing lead with at least one pacing electrode, a controller, a lumen, a reservoir, and a pump, wherein the method comprises:
   treating a cardiac condition using the implantable medical device by providing an autologous respiration-competent mitochondria at programmed intervals and providing electrical pacing to a patient's heart via a pulse generator having a pacing lead including a pacing electrode,
   wherein providing electrical pacing includes generating and delivering the electrical pulses to cardiac tissue of the patient using the pulse generator and the pacing lead, and controlling timing of the delivered electrical pulses using the controller to cause the cardiac tissue to contract with a specified AV delay to reduce wall stress during contraction in cardiac tissue proximate to the pacing electrode in the patient's heart by causing cardiac tissue proximate to the pacing electrode to contract against a reduced preload,
   wherein providing the autologous respiration-competent mitochondria at programmed intervals includes providing the autologous respiration-competent mitochondria, using the controller and the pump, from the reservoir through the lumen to the patient's cardiac tissue proximate to the pacing electrode, wherein the patient's cardiac tissue proximate to the pacing electrode, which has the reduced wall stress during contraction, is a more hospitable location for integration of the autologous respiration-competent mitochondria with the cardiac tissue, and
   wherein controlling timing of the delivered electrical pulses includes increasing the AV delay for a predetermined time interval each time when the autologous respiration-competent mitochondria is provided to the patient's cardiac tissue.

11. The method of claim 10, wherein providing the electrical pacing includes providing a cardiac resynchronization therapy (CRT).

12. The method according to claim 10, further comprising providing a diluent or adjuvant to the implanted reservoir to preserve the respiration-competent mitochondria within the implanted reservoir.

13. The method according to claim 10, wherein the autologous mitochondria are provided to promote and augment cellular regeneration and/or myocardiocyte growth initiated by the presence of the pacing lead.

14. The method according to claim 10, wherein the autologous mitochondria are provided by at least two endocardial injection sites to increase the density of de novo trabecular cardiomyocyte fiber growth.

15. The method according to claim 10, wherein the pacing lead is configured to promote de novo trabecular fiber attachment.

16. The method according to claim 10, further comprising providing an electrical waveform to the patient's cardiac tissue having the reduced wall stress to further promote cellular regeneration or myocardiocyte growth.

17. The method of claim 10, wherein the pacing lead includes the lumen configured to deliver the autologous respiration-competent mitochondria.

* * * * *